(12) United States Patent
Farra

(10) Patent No.: US 12,420,011 B2
(45) Date of Patent: Sep. 23, 2025

(54) DEVICES AND METHODS FOR FLOW RESTRICTION IN A MICROFLUIDIC CIRCUIT FOR DRUG DELIVERY

(71) Applicant: Cequr SA, Horw (CH)

(72) Inventor: Robert Farra, Action, MA (US)

(73) Assignee: Cequr SA, Horw (CH)

( * ) Notice: Subject to any disclaimer, the term of this patent is extended or adjusted under 35 U.S.C. 154(b) by 999 days.

(21) Appl. No.: 16/964,360

(22) PCT Filed: Feb. 15, 2019

(86) PCT No.: PCT/IB2019/000150
§ 371 (c)(1),
(2) Date: Jul. 23, 2020

(87) PCT Pub. No.: WO2019/158997
PCT Pub. Date: Aug. 22, 2019

(65) Prior Publication Data
US 2021/0030952 A1    Feb. 4, 2021

Related U.S. Application Data

(60) Provisional application No. 62/631,522, filed on Feb. 16, 2018.

(51) Int. Cl.
*A61M 5/168* (2006.01)
*A61K 38/28* (2006.01)
(Continued)

(52) U.S. Cl.
CPC ......... *A61M 5/16804* (2013.01); *A61K 38/28* (2013.01); *A61M 5/14248* (2013.01);
(Continued)

(58) Field of Classification Search
CPC .... A61M 5/14248; A61M 2005/14252; A61M 5/1424; A61M 2005/1585; A61M 5/158;
(Continued)

(56) References Cited

U.S. PATENT DOCUMENTS 5,009,251 A    4/1991  Pike et al.
5,839,467 A    11/1998  Saaski et al.
(Continued)

FOREIGN PATENT DOCUMENTS

WO    03000416 A2    1/2003
WO    2015114635 A1    8/2015

OTHER PUBLICATIONS

International Search Report and Written Opinion for International Application No. PCT/IB2019/000150, dated May 22, 2019, 16 pages.
(Continued)

*Primary Examiner* — Michael J Tsai
*Assistant Examiner* — Kathleen Paige Farrell
(74) *Attorney, Agent, or Firm* — Eversheds Sutherland (US) LLP

(57) ABSTRACT

A device for administering a liquid drug formulation to a patient is disclosed. The device includes a reservoir configured to hold a quantity of a liquid drug formulation and a microfluidic circuit that includes at least one flow path configured to transport the liquid drug formulation from the reservoir to a drug release outlet. The microfluidic circuit includes at least one flow restrictor in the at least one flow path. The at least one flow restrictor includes a first substrate secured to a second substrate with a flow channel formed into at least one of the first substrate and the second substrate, and disposed between the first substrate and the second substrate.

21 Claims, 5 Drawing Sheets

(51) Int. Cl.
*A61M 5/142* (2006.01)
*A61M 5/152* (2006.01)

(52) U.S. Cl.
CPC ..... *A61M 5/152* (2013.01); *A61M 2205/0244* (2013.01); *A61M 2205/3331* (2013.01); *A61M 2205/7545* (2013.01); *A61M 2207/00* (2013.01)

(58) Field of Classification Search
CPC ...... A61M 5/14244; A61M 2205/3334; A61M 5/16886; A61M 2205/3344; A61M 5/3287; A61M 5/16854; A61M 2205/3331; A61M 2205/0244; A61M 5/141; A61M 2205/3358; A61M 2207/00; A61M 5/16804; A61M 5/152; A61M 2205/7545; A61K 38/28
See application file for complete search history.

(56) References Cited

U.S. PATENT DOCUMENTS

| | | | |
|---|---|---|---|
| 6,619,311 B2 | 9/2003 | O'Connor et al. | |
| 6,644,944 B2 | 11/2003 | Karp | |
| 6,845,787 B2 | 1/2005 | Karp et al. | |
| 6,845,968 B2 | 1/2005 | Killeen et al. | |
| 6,857,449 B1 | 2/2005 | Chow | |
| 6,878,271 B2 * | 4/2005 | Gilbert | C30B 7/00 216/2 |
| 6,890,093 B2 | 5/2005 | Karp et al. | |
| 7,108,354 B2 | 9/2006 | Gulvin et al. | |
| 7,250,775 B1 | 7/2007 | Collins et al. | |
| 7,431,052 B2 | 10/2008 | Gravesen et al. | |
| 7,517,335 B2 | 4/2009 | Gravesen et al. | |
| 7,520,295 B2 | 4/2009 | Rasmussen et al. | |
| 7,603,898 B2 | 10/2009 | Speldrich | |
| 7,632,247 B2 | 12/2009 | Adams | |
| 7,713,258 B2 | 5/2010 | Adams et al. | |
| 7,713,262 B2 | 5/2010 | Adams et al. | |
| 7,771,391 B2 | 8/2010 | Carter | |
| 7,815,609 B2 | 10/2010 | Hines et al. | |
| 7,846,132 B2 | 12/2010 | Gravesen et al. | |
| 7,887,756 B2 | 2/2011 | McAvoy et al. | |
| 7,927,306 B2 | 4/2011 | Cross et al. | |
| 7,931,621 B2 | 4/2011 | Cross et al. | |
| 7,938,801 B2 | 5/2011 | Hawkins et al. | |
| 7,976,493 B2 | 7/2011 | Carter et al. | |
| 7,976,500 B2 | 7/2011 | Adams et al. | |
| 7,976,505 B2 | 7/2011 | Hines et al. | |
| 8,062,256 B2 | 11/2011 | Carter et al. | |
| 8,109,912 B2 | 2/2012 | Alferness et al. | |
| 8,114,064 B2 | 2/2012 | Alferness et al. | |
| 8,128,596 B2 | 3/2012 | Carter | |
| 8,128,597 B2 | 3/2012 | Cross et al. | |
| 8,162,923 B2 | 4/2012 | Adams et al. | |
| 8,226,606 B2 | 7/2012 | Adams et al. | |
| 8,226,607 B2 | 7/2012 | Carter et al. | |
| 8,230,744 B2 | 7/2012 | Gravesen et al. | |
| 8,231,572 B2 | 7/2012 | Carter et al. | |
| 8,231,577 B2 | 7/2012 | Carter et al. | |
| 8,246,581 B2 | 8/2012 | Adams et al. | |
| 8,361,030 B2 | 1/2013 | Carter | |
| 8,409,151 B2 | 4/2013 | Hawkins et al. | |
| 8,449,504 B2 | 5/2013 | Carter et al. | |
| 8,540,673 B2 | 9/2013 | Hines et al. | |
| 8,547,239 B2 | 10/2013 | Peatfield et al. | |
| 8,613,719 B2 | 12/2013 | Karratt et al. | |
| 8,672,873 B2 | 3/2014 | Gravesen et al. | |
| 8,679,694 B2 | 3/2014 | Zimmermann et al. | |
| 8,696,630 B2 | 4/2014 | Carter et al. | |
| 8,753,315 B2 | 6/2014 | Alferness et al. | |
| 8,758,308 B2 | 6/2014 | Alferness et al. | |
| 8,894,612 B2 | 11/2014 | Hawkins et al. | |
| 8,905,974 B2 | 12/2014 | Carter et al. | |
| 8,945,064 B2 | 2/2015 | Gravesen et al. | |
| 9,005,169 B2 | 4/2015 | Gravesen et al. | |
| 9,022,972 B2 | 5/2015 | Gravesen et al. | |
| 9,039,654 B2 | 5/2015 | Gravesen et al. | |
| 9,174,009 B2 | 11/2015 | Peatfield et al. | |
| 9,211,378 B2 | 12/2015 | Bolt et al. | |
| 9,387,288 B2 | 7/2016 | Karratt et al. | |
| 9,651,039 B2 | 5/2017 | Mathies et al. | |
| 9,694,147 B2 | 7/2017 | Peatfield et al. | |
| 9,713,674 B2 | 7/2017 | Carter et al. | |
| 9,968,747 B2 | 5/2018 | Gravesen et al. | |
| 10,226,588 B2 | 3/2019 | Peatfield et al. | |
| 10,258,741 B2 | 4/2019 | Gravesen et al. | |
| 2002/0022798 A1 * | 2/2002 | Connelly et al. | A61M 5/16881 |
| 2002/0053242 A1 | 5/2002 | Tai et al. | |
| 2002/0097303 A1 | 7/2002 | Gulvin et al. | |
| 2002/0117517 A1 | 8/2002 | Unger et al. | |
| 2002/0127736 A1 | 9/2002 | Chou et al. | |
| 2003/0073952 A1 * | 4/2003 | Flaherty et al. | A61M 5/14248 |
| 2003/0116738 A1 | 6/2003 | O'Connor et al. | |
| 2004/0086427 A1 | 5/2004 | Childers et al. | |
| 2004/0153029 A1 | 8/2004 | Blischak et al. | |
| 2004/0209354 A1 | 10/2004 | Mathies et al. | |
| 2005/0279635 A1 | 12/2005 | Chow et al. | |
| 2007/0028683 A1 | 2/2007 | Ionescu-Zanetti | |
| 2007/0224084 A1 | 9/2007 | Holmes et al. | |
| 2008/0249510 A1 * | 10/2008 | Mescher | A61M 31/002 604/890.1 |
| 2009/0090172 A1 * | 4/2009 | Angelescu et al. | G01N 11/08 |
| 2009/0129952 A1 | 5/2009 | Patrascu et al. | |
| 2009/0317298 A1 | 12/2009 | McAvoy et al. | |
| 2010/0018584 A1 | 1/2010 | Bransky et al. | |
| 2011/0066108 A1 * | 3/2011 | Geipel | A61M 5/16877 137/557 |
| 2012/0101451 A1 * | 4/2012 | Boit | A61M 39/223 417/490 |
| 2012/0228238 A1 * | 9/2012 | Van Rijn et al. | A61M 15/00 |
| 2013/0217598 A1 | 8/2013 | Ludwig et al. | |
| 2014/0197101 A1 * | 7/2014 | Harjes et al. | A61M 1/16 |
| 2014/0311912 A1 | 10/2014 | Shih et al. | |
| 2015/0367066 A1 | 12/2015 | Gravesen et al. | |
| 2016/0008536 A1 | 1/2016 | Gravesen et al. | |
| 2016/0038940 A1 | 2/2016 | Babcock | |
| 2017/0191892 A1 | 7/2017 | Winzeler et al. | |
| 2017/0246383 A1 * | 8/2017 | Lanier, Jr. | F04B 17/00 |
| 2020/0069887 A1 * | 3/2020 | Ross | A61M 5/14248 |

OTHER PUBLICATIONS

International Search Report of International Application No. PCT/IL2015/050111 dated Jul. 7, 2015 (11 pages).

* cited by examiner

DEVICES AND METHODS FOR FLOW RESTRICTION IN A MICROFLUIDIC CIRCUIT FOR DRUG DELIVERY

CROSS-REFERENCE TO RELATED APPLICATIONS

This application claims priority to and the benefit of U.S. provisional patent application No. 62/631,522, filed Feb. 16, 2018, which is incorporated herein by reference in its entirety.

FIELD OF THE DISCLOSURE

The disclosure relates generally to systems and methods for controlling flow in a microfluidic circuit, and more particularly to a microfluidic circuit of a drug delivery device, for example a wearable patch pump for administration of insulin.

BACKGROUND

Drug delivery pumps may provide a user (a patient) with constant basal delivery, and bolus dosing, of a drug (e.g., insulin). A conventional system of controlling the flow rate in a microfluidic circuit of an insulin pump, for example, may include a pressure source combined with a flow restrictor. In some embodiments, such as those disclosed in U.S. Pat. No. 7,520,295 to Rasmussen et al., the flow restrictor is a capillary tube with a known internal diameter and length.

However, fabricating suitable capillary tubes is not a simple process. It requires precisely determining the internal diameter of the capillary tube, cutting the capillary tube to the appropriate length based on the internal diameter, which may vary due to manufacturing limitations, and chemically etching the ends of the capillary tube. For example, the internal diameter of a capillary tube must be measured through a polyimide coating with submicron precision. Cleanly cutting the capillary tube without producing fractures or creating possible contaminants that can become trapped inside the capillary tube is difficult. As a result, the ends of the capillary tube need to be chemically etched and cleaned. In addition, capillary tubes are notoriously difficult to handle without breakage. The fabrication process thus requires custom equipment and fixtures, and/or the development of high-speed automation equipment capable of handling individual capillary tubes.

It therefore would be desirable to provide suitable flow restriction without the challenges associated with the inclusion of capillary tubes.

SUMMARY

Some or all of the above needs and/or problems may be addressed by the devices, systems, and methods disclosed herein.

In one aspect, devices are provided for administering a liquid drug formulation to a patient. The device includes (i) a reservoir configured to hold a quantity of the liquid drug formulation; and (ii) a microfluidic circuit which comprises at least one flow path configured to transport the liquid drug formulation from the reservoir to a drug release outlet. The microfluidic circuit include at least one flow restrictor in the at least one flow path. The at least one flow restrictor includes a first substrate secured to a second substrate with a flow channel, e.g., a microfabricated flow channel, that is formed into at least one of the first and second substrates and that is disposed between the first and second substrates.

In another aspect, methods are provided for forming a microfluidic circuit of a drug delivery device, wherein the microfluidic circuit includes one or more flow restrictors, each of which includes a first substrate secured to a second substrate with a flow channel, e.g., a microfabricated flow channel, that is formed into at least one of the first and second substrates and that is disposed between the first and second substrates.

In still another aspect, methods are provided for administering a drug to a patient using a drug delivery device having a microfluidic circuit that includes one or more flow restrictors, each of which includes a first substrate secured to a second substrate with a flow channel, e.g., a microfabricated flow channel, that is formed into at least one of the first and second substrates and that is disposed between the first and second substrates.

Other aspects of the flow restrictors, their methods of manufacture, and their methods of use are also described herein.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in certain embodiments. Elements and/or components in the figures are not necessarily drawn to scale. Throughout this disclosure, depending on the context, singular and plural terminology may be used interchangeably.

DETAILED DESCRIPTION

Figure 1A:
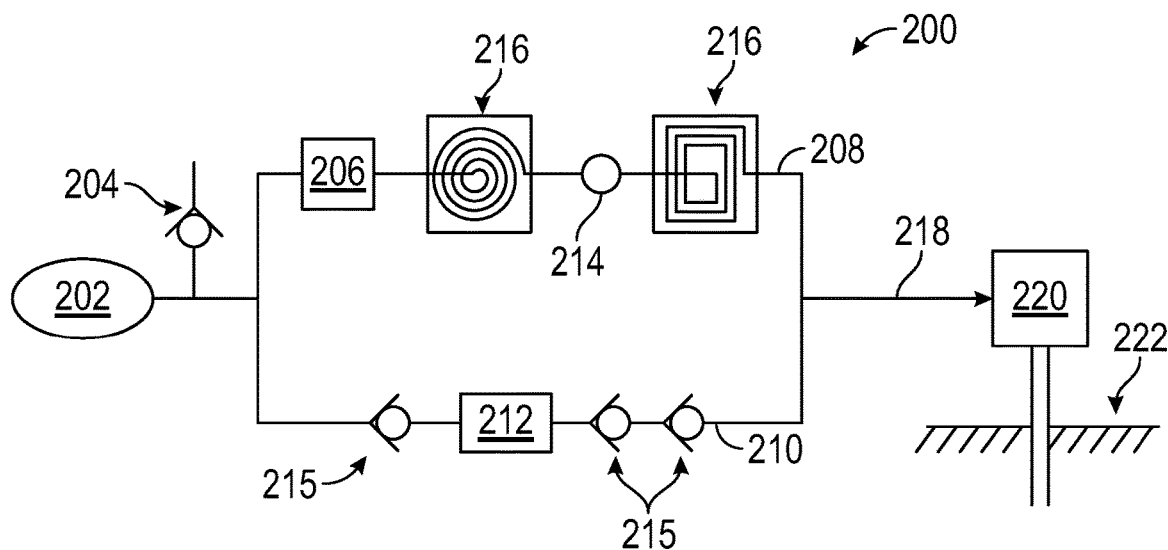
FIG. 1A depicts a microfluidic circuit of a fluid drug delivery device in accordance with one embodiment of the present disclosure.

Device and methods have been developed that include (i) a reservoir configured to hold a quantity of the liquid drug formulation; and (ii) a microfluidic circuit which comprises at least one flow path configured to transport the liquid drug formulation from the reservoir to a drug release outlet, wherein the microfluidic circuit includes at least one flow restrictor in the at least one flow path, and wherein the at least one flow restrictor includes a first substrate secured to a second substrate with a flow channel formed into at least one of the first and second substrates and disposed between the first and second substrates. In this way, the flow channel is defined by, i.e., bounded by, the first and second substrates. In a preferred embodiment, the flow channel is a microfabricated flow channel. These flow restrictors, including those with a microfabricated flow channel—which may be referred to herein as micro-electromechanical system (MEMS)-type flow restrictors—advantageously obviate the need to include glass capillary tubes in the microfluidic circuit.

In some particular embodiments, the devices and methods including these MEMS-type flow restrictors are part of a pump device, such as a wearable patch pump. For example, the pump device may be an insulin pump for bolus-only insulin administration or for both basal and bolus insulin administration.

As used herein, the term "flow restrictor" refers to a component structured to throttle, or limit, a flow of fluid through a microfluidic circuit. It is neither a valve nor operable to shut off the flow of fluid. In some embodiments, the flow restrictor includes one or more channels having passages reduced in size relative to other passages in the microfluidic circuit, such that the dimensions (cross-sectional area and length) are selected to provide a limit on the rate of flow of fluid therethrough for a given range of fluid pressures on the supply side of the restrictor. To be clear, a microcapillary, such as one produced by drawing or extruding glass tubes, is not a flow restrictor as described and claimed herein.

The present "flow restrictor" may be produced using MEMS fabrication techniques and materials, and it therefore may be referred to herein as a "MEMS flow restrictor." The presently disclosed flow restrictor also may be produced using other suitable manufacturing techniques known in the art, such as additive manufacturing (e.g., 3D-printing) methods and systems.

In one aspect, a device is provided for administering a liquid drug formulation to a patient. In some embodiments, the device includes (i) a reservoir configured to hold a quantity of a liquid drug formulation; and (ii) a microfluidic circuit which comprises at least one flow path configured to transport the liquid drug formulation from the reservoir to a drug release outlet, wherein the microfluidic circuit comprises one or more flow restrictors in the at least one flow path, and wherein the flow restrictors each include a first substrate secured to a second substrate with a flow channel that is (i) formed into the first and/or second substrates, and (ii) disposed between the first and second substrates. The flow channel may be formed by a microfabrication process.

In some embodiments, a MEMS flow restrictor is formed by two substrates (e.g., substantially planar structures) attached to each other. That is, the flow channel of the flow restrictor may be defined/bounded by the two substrates. For example, a flow channel having selected dimensions may be microfabricated into a first substrate. That is, the flow channel may be formed using a microfabrication process e.g., including masking and etching steps known in the art. The dimensions of the flow channel are selected to provide a calculated restriction of (resistance to) the flow of a known fluid therethrough, for example, an insulin solution or other selected liquid drug formulation. The flow channel may be a micro-flow channel. Then, the first substrate with the flow channel etched, or otherwise formed, therein is fixed to a second substrate, such that the elongated opening of the channel in the first substrate is sealed by the second substrate. In some embodiments, each of the opposed open ends of the flow channel serves as an inlet or an outlet to the flow channel, and thus as an inlet and an outlet of the flow restrictor. In some embodiments, the inlet and the outlet each extend through an opening in the first substrate. In some embodiments, the second substrate includes an inlet and an outlet to the flow channel. For example, the inlet and the outlet may be etched or otherwise formed to extend through the second substrate. In some other embodiments, the inlet and the outlet to the flow channel are disposed in one or more sides of the first substrate.

In some embodiments, the second substrate includes no openings and no portion of the flow channel. For example, it may have a planar surface that mates against the first substrate, like a lid, closing off the elongate side opening of the flow channel formed into the first substrate. In some other embodiments, the second substrate includes one more flow channels or portions thereof. These flow channels or portions thereof may be open to, and/or may define part of the flow channel in the first substrate.

In some embodiments, the flow channel in the first substrate has a closed, elongated bottom wall, an elongated (lateral) opening in a planar surface of the first substrate opposed to the bottom wall, and a pair of elongated sidewalls extending between the bottom wall of the flow channel and the elongated opening. The elongated opening are closed off by the second substrate.

In some embodiments, the flow restrictor is formed of more than two substrates, e.g., a stack of three, four, or more substrates. For example, in some cases it may be desirable to construct the channels to lie in two or more parallel planes, for example, with orthogonal connecting passages. For example, the restrictor may include a stack of three substrates with a first portion of the flow channel defined by/between an upper substrate and a middle substrate, and a second portion of the flow channel defined by/between the middle substrate and a lower substrate. Such embodiments may be useful where the lateral area of the flow restrictor needs to be conserved without sacrificing the length of the flow channel, and increasing the height of the flow restrictor is acceptable.

In some embodiments, the inlet, the outlet, or both the inlet and the outlet, is/are tapered to help manage the passage of air bubbles through the flow channel and thereby reduce the chance of bubbles interfering with the desired flow of the drug-containing liquid through the flow channel. In typical embodiments, the taper is such that the cross-sectional area of the opening is larger at the outer edge/distal ends of the flow channel than within the body of the channel. That is, at the inlet end, the inner diameter narrows going into the flow channel and widens coming out of the outlet end.

The substrates may be constructed of any suitable material. The substrates may include or consist of a single material or may comprise two or more different materials, e.g., as a multi-layered or other composite structure. In some embodiments, the substrates include a coating material on the surfaces defining the flow channels, i.e., the surfaces in contact with the fluid flowing therethrough. In some embodiments, the substrates are formed of one or more biocompatible metals, glasses, ceramic materials, and/or polymers. Some non-limiting examples of suitable materials of construction include silicon, aluminum oxide, polydimethylsiloxane (PDMS), polycarbonate, polymethylmethacrylate, and polytetrafluorethylene.

In some embodiments, the substrates are formed of one or more materials suitable for use in MEMS microfabrication processes, such as silicon, gold, silicon nitride, silicon dioxide.

Generally, at least the portion of the substrates in contact with the fluid flowing through the flow channel, e.g., an aqueous solution comprising insulin, is compatible with the fluid. That is, contact between the fluid and the flow restrictor imparts no detectable or undesirable change in the fluid and causes no detectable change in the flow restrictor's performance during the useful life of the flow restrictor.

In some embodiments, the first and second substrates are silicon. In some embodiments, the first and second substrates are a glass. The first substrate may be made of the same material as that of the second substrate, or the materials of the first and second substrates may be different from one another. The substrates may be any suitable size, shape, or configuration. In some instances, the two substrates are sealed together using anodic bonding or the like. Any suitable sealing process or technique known in the art may be used to secure the first and second substrates together.

The geometry of the flow channel may take a variety of forms. In some embodiments, the flow channel is composed of a plurality of linear segments and angled or curved connecting segments joining the linear segments together. In other embodiments, the flow channel is composed of a plurality of curved segments, of varying radii of curvature. In various examples, the flow channel may form a serpentine pattern, a decreasing/increasing spiral pattern, a decreasing/increasing square spiral pattern, or a combination thereof, across the substrate. The depth of the flow channel may be constant or variable within the flow restrictor. The sidewalls of the channel may be straight, tapered, or curved. The flow channel may be essentially any size, shape, or configuration that meets the desired flow restriction characteristics. In some embodiments, the geometry of the flow channel is provided in a dense pattern that utilizes the least lateral substrate area, since minimizing the substrate area can help minimize the cost of the substrate needed to produce the desired flow restrictor. For example, a decreasing/increasing square flow channel shape may be ideally suited for maximizing the number of substrates per silicon wafer, and thus minimizing the substrate cost.

In one exemplary embodiment, the first and second substrates are substantially square. For example, in one case, the substrates are about 2 mm×2 mm, with a thickness of about 0.3 mm and a combined thickness of about 0.75 mm. At least one dimension of the microfluidic circuit (e.g., the diameter or width) may be in the range of about a micrometer to tens of micrometers. The flow channel of the flow restrictor may be about 20 microns wide and may include a serpentine pattern or a decreasing/increasing square spiral.

In another exemplary embodiment, multiple MEMS flow restrictors are formed within/between a pair of substrates, e.g., by the first and second substrates described above.

For example, two or more separate flow channels can be formed on the first substrate, and two respective inlets and outlets may be formed on the second substrate.

In some embodiments, a flow channel of the microfluidic circuit is in operable communication with a sensor, such as a pressure sensor or a flow sensor, configured to measure or detect a characteristic of a fluid flowing through the flow channel. The sensor may be an absolute pressure sensor, a gauge pressure sensor, a differential pressure sensor, a sealed pressure sensor, a piezoresistive strain gauge, or the like. For example, the pressure sensor may measure the strain (or deflection) of a diaphragm, a piston, a bourdon tube, or a bellows. Any suitable pressure sensor may be used. The sensor may be a separately formed component, or it may be integrally formed with a MEMS flow restrictor as described herein.

In some embodiments, for example, a pressure sensing membrane is integrally formed with the first substrate, the second substrate, or a combination thereof. The pressure sensing membrane may be disposed between two MEMS flow restrictors. For instance, the first and second substrates may include two microfluidic circuits, e.g., two separate flow channels, with an integral pressure sensor, which may be operably disposed therebetween. The benefit of this configuration is that the fluidic circuit controlling and monitoring the flow is comprised of one integral component without relying on plastic housing features, elastomeric membranes, or external pressure transducers, which may be expensive and/or unreliable. In addition, this configuration may be considerably less expensive to produce due to the consolidation of components.

The flow restrictors may be manufactured by photolithography and etching or other MEMS processes and techniques, which enables mass production at relatively low cost. For example, a 200 mm silicon wafer can produce about 3,000 substrates. In addition, once the MEMS manufacturing process is validated, then in-process inspections may not required, thereby further reducing production costs.

In a preferred embodiment, the configuration of the flow restrictor ensures that the flow of fluid through the restrictor is laminar flow. For example, the tapered inlets and outlets of the flow channel and the dimensions of the channel facilitate laminar flow. The flow restrictors also enable a laminar flow through the remainder of the microfluidic circuit by limiting the flow rate therethrough.

The flow channels optionally may include a lubricious coating. Suitable such coating materials are known in the art and may be added to the flow channels to facilitate air purging and/or fluid circuit priming.

Turning now to the drawings, FIGS. 1A, 1B, 2, and 3 show schematic diagrams of several possible different microfluidic circuits of a drug delivery device for administration of a liquid drug formulation, wherein the circuits include a flow restrictor as described herein. In one case, the drug delivery device is an insulin pump, such as a wearable patch pump for bolos and/or basal administration of insulin. Microfluidic circuits having other configurations, or utilizing (or omitting) any number of other components, may incorporate the one or more MEMS flow restrictors disclosed herein. For example, U.S. Pat. Nos. 7,517,335; 8,672,873; and 8,547,239 describe various alternative microfluidic circuits for a patch pump or the like. Those patents are incorporated herein by reference.

The illustrated microfluidic circuits may be packaged in a device housing that is configured to be worn a patient's skin, e.g., a patch pump. In a preferred embodiment, the patch pump is an insulin pump. To make the patch pump wearable, the housing may include a pressure-sensitive adhesive or other means suited to releasably secure the device to the patient's skin.

Figure 1B:
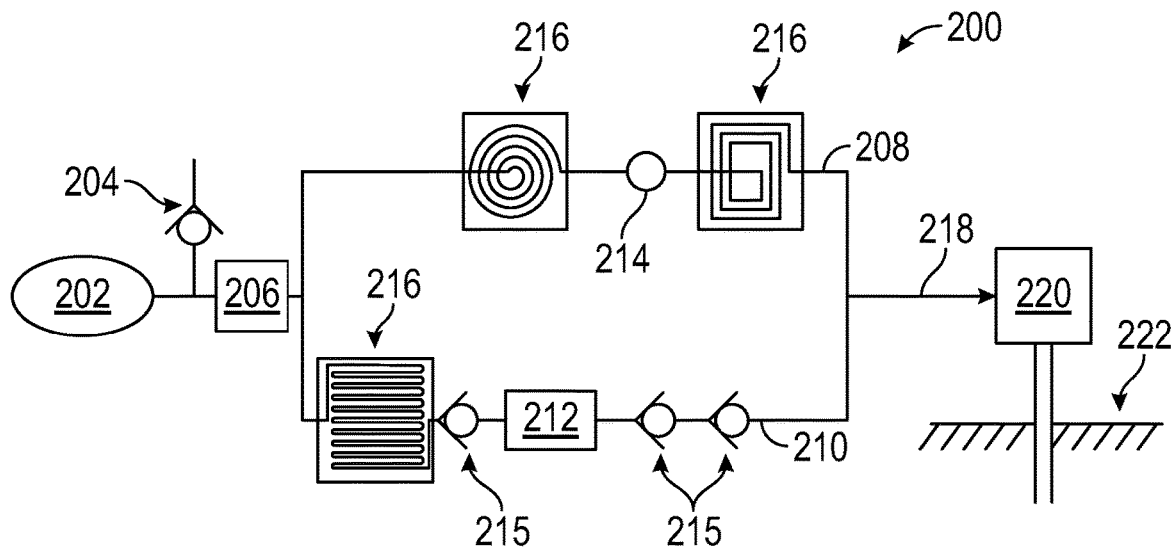
FIG. 1B depicts a microfluidic circuit of a fluid drug delivery device in accordance with another embodiment of the present disclosure.

FIGS. 1A and 1B illustrate a microfluidic circuit 200 that incorporates two (FIG. 1A) or three (FIG. 1B) flow restrictors. In the illustrated embodiments, the microfluidic circuit 200 includes a reservoir 202 configured to hold a quantity of insulin or another suitable liquid drug formulation. In some embodiments, the reservoir 202 comprises an elastomeric bladder. A fill port 204 is used to introduce the drug formulation into the microfluidic circuit 200. Introducing the drug formulation via the fill port 204 fills the reservoir 202, elastically expanding the elastomeric bladder.

During use, the insulin or other suitable liquid drug formulation is forced from the reservoir 202, due to forces imparted by contraction of the elastomeric bladder returning to its natural (unloaded) state, into two parallel flow paths. The first flow path is a basal flow path 208, and the second flow path is a bolus flow path 210. In certain embodiments, as depicted in FIG. 1A, a filter 206 is disposed in the basal flow path 208.

In other instances, as depicted in FIG. 1B, the filter 206 is configured to filter fluid in both the basal flow path 208 and the bolus flow path 210. In the illustrated embodiment, the filter 206 is located upstream of both the basal flow path 208 and the bolus flow path 210.

The basal flow path 208 is configured to deliver a constant, continuous, dose of insulin to a user. The user typically is a human patient in need of the drug. The bolus flow path 210 is configured to intermittently, e.g., on-demand, deliver a bolus dose of insulin to the user, as needed or desired by the user, upon actuation of a bolus delivery system 212 via a bolus button or the like. Any number of systems and methods may be used to deliver the bolus dose via the bolus flow path 210. In some alternative embodiments, the bolus flow path 210 is omitted. In some other alternative embodiments, the basal flow path 208 is omitted.

In the illustrated embodiments, the basal flow path 208 includes a pressure sensor 214 or other flow sensor in communication with the basal flow path 208.

One or more flow restrictors 216 as described herein may be disposed in the basal flow path 208 and/or in the bolus flow path 210. In some instances, as depicted in FIG. 1A, the flow restrictor 216 disposed in the bolus flow path 210 is omitted. In such instances, the filter 206 may be disposed in the basal flow path 208. The flow restrictors 216 are configured to limit the rate of fluid flow through the basal flow path 208 and/or the bolus flow path 210. One or more of the flow restrictors 216 shown in FIGS. 1A-1B may be or include MEMS flow restrictors.

In the illustrated embodiments, the basal flow path 208 includes two flow restrictors 216 in series. A pressure sensor 214 is disposed between the flow restrictors 216 in the basal flow path 208. Additional flow restrictors 216 may be disposed in the basal flow path 208. In some alternative embodiments, the flow restrictors 216 is omitted from the basal flow path 208.

Although not necessarily favored for the reasons described in the background above, in some instances, one or more capillary tubes may be combined with the flow restrictors 216 to control the flow of fluid through the microfluidic circuit 200.

In FIG. 1B, the bolus flow path 210 includes a flow restrictor 216 disposed upstream of the bolus delivery system 212 in the bolus flow path 210. In this embodiment, the filter 206 is disposed upstream of the bolus flow path 210 to filter the fluid before it enters the flow restrictor 216. Additional flow restrictors 216 may be disposed in the bolus flow path 210 upstream and/or downstream of the bolus delivery system 212. As shown in FIG. 1A, the flow restrictor 216 may be omitted from the bolus flow path 210.

One or more check valves 215 may be disposed in one or both of the basal flow path 208 and the bolus flow path 210. In some embodiments, at least one check valve 215 is disposed in the bolus flow path 210 at each of a position upstream and downstream of the bolus delivery system 212.

In the illustrated embodiment, one check valve 215 is disposed upstream of the bolus delivery system 212 in the bolus flow path 210, and two check valves 215 are disposed downstream of the bolus delivery system 212 in the bolus flow path 210.

The pressure required to open the check valve 215 downstream of the bolus delivery system 212 in the bolus flow path 210 is typically greater than the pressure of the reservoir 202, i.e., the fluid pressure produced by the reservoir's force of contraction, and the bolus delivery system 212 is configured to generate a pressure effective to open the check valve 215 downstream of the bolus delivery system 212. In some alternative embodiments, the check valves 215 are omitted. In some other alternative embodiments, the check valves 215 are replaced with one or more multi-position valves.

The parallel basal flow path 208 and the bolus flow path 210 join at a common channel 218, upstream of a cannula 220. The cannula 220 extends into/through the skin 222 of the user. In this way, the microfluidic circuit 200 provides a flowpath from the reservoir to user, for controlled delivery of the insulin or other fluid drug formulation subcutaneously to the user.

The microfluidic circuit 200 may include additional components. Conversely, certain components may be omitted. In any case, the microfluidic circuit 200 is configured to deliver one or more drugs in a liquid vehicle, e.g., as a solution or suitable suspension of a drug dissolved or dispersed in a pharmaceutically acceptable liquid excipient vehicle. The devices and systems described herein can be used to deliver essentially any suitable pharmaceutical agent for therapeutic, prophylactic, diagnostic, or palliative purposes.

Figure 2:
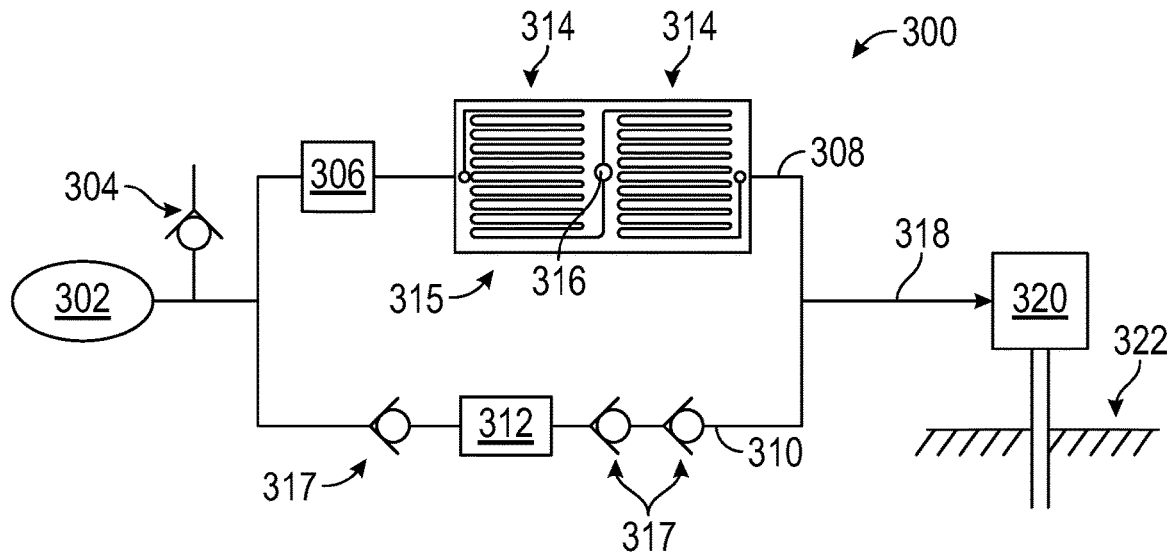
FIG. 2 depicts a microfluidic circuit of a fluid drug delivery device in accordance with yet another embodiment of the present disclosure.
Figure 3:
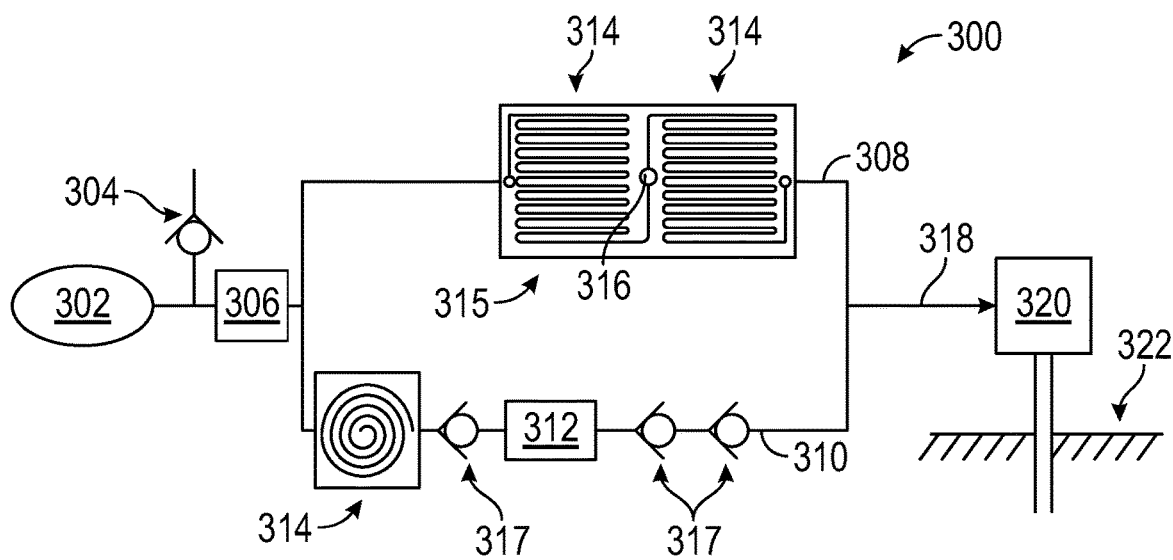
FIG. 3 depicts a microfluidic circuit of a fluid drug delivery device in accordance with still another embodiment of the present disclosure.

FIGS. 2 and 3 depict another microfluidic circuit 300 of a fluid drug delivery device that incorporates the flow restrictors described herein. One or more of the flow restrictors 314 shown in FIGS. 2-3 may be or include MEMS flow restrictors.

In the illustrated embodiments, the microfluidic circuit 300 includes a reservoir 302 configured to hold a quantity of insulin or another suitable liquid drug formulation. In some embodiments, the reservoir 302 comprises an elastomeric bladder. A fill port 304 is included to introduce the drug formulation into the microfluidic circuit 300. Introducing the drug formulation via the fill port 304 fills the reservoir 302, elastically expanding the elastomeric bladder.

During use, the insulin or other suitable liquid drug formulation is forced from the reservoir 302, due to forces imparted by contraction of the elastomeric bladder returning to its natural (unloaded) state, into two parallel flow paths. The first flow path is a basal flow path 308, and the second flow path is a bolus flow path 310. As depicted in FIG. 2, a filter 306 is disposed in the basal flow path 308.

In other instances, as depicted in FIG. 3, the filter 306 is configured to filter fluid in both the basal flow path 308 and the bolus flow path 310. For example, the filter 306 is located upstream of both the basal flow path 308 and the bolus flow path 310.

The basal flow path 308 is configured to deliver a constant, continuous, dose of insulin to a user. The user typically is a human patient in need of the drug. The bolus flow path 310 is configured to intermittently, e.g., on-demand, deliver a bolus dose of insulin to the user, as needed or desired by the user, upon actuation of a bolus delivery system 312 via a bolus button or the like. Any number of systems and methods may be used to deliver the bolus dose via the bolus flow path 310. In some instances, the bolus flow path 310 is omitted. In some other instances, the basal flow path 308 is omitted.

One or more check valves 317 may be disposed in one or both of the basal flow path 308 and the bolus flow path 310. In some embodiments, at least one check valve 317 is disposed in the bolus flow path 310 at each of a position upstream and downstream of the bolus delivery system 312. In the illustrated embodiments, one check valve 317 is disposed upstream of the bolus delivery system 312 in the bolus flow path 310, and two check valves 317 are disposed downstream of the bolus delivery system 312 in the bolus flow path 310.

The pressure required to open the check valve 317 downstream of the bolus delivery system 312 in the bolus flow path 210 is typically greater than the pressure of the reservoir 302, i.e., the fluid pressure produced by the reservoir's force of contraction, and the bolus delivery system 312 is configured to generate a pressure effective to open the check valve 317 downstream of the bolus delivery system 312. In some alternative embodiments, the check valves 317 are omitted. In some other alternative embodiments, the check valves 317 are replaced with one or more multi-position valves.

Flow restrictors 314 are configured to limit the rate of fluid flow through the basal flow path 308 and/or the bolus flow path 310. In the embodiments illustrated in FIGS. 2 and 3, two flow restrictors 314 are disposed in the basal flow path 308. In FIG. 3, one flow restrictor 312 is disposed in the bolus flow path 310. In FIG. 2, no flow restrictors 314 is disposed in the bolus flow path 310. In FIG. 2, a filter 306 is located in the basal flow path 308 upstream of the flow restrictors 314. In these illustrated embodiments, the basal flow path 308 includes two MEMS flow restrictors 314 with an integral pressure sensor 316 combined into a single MEMS device 315. The two MEMS flow restrictors 314 of the MEMS device 315 are disposed in series in the basal flow path 308, and the pressure sensor 316 is disposed between the MEMS flow restrictors 314 in the basal flow path 308.

In other embodiments, the MEMS device 315 may include additional MEMS flow restrictors 314 integrated therein. Alternatively or in addition, the basal flow path 308 may include other flow restrictors 314. In some alternative embodiments, the MEMS flow restrictors 314 is omitted from the basal flow path 308.

Although not necessarily favored for the reasons described in the background above, in some instances, one or more capillary tubes may be combined with the flow restrictors 314 to control the flow of fluid through the microfluidic circuit 300.

In certain embodiments, as depicted in FIG. 3, the bolus flow path 310 includes a flow restrictor 314 disposed upstream of the bolus delivery system 312 in the bolus flow path 310. The flow restrictor may be a MEMS flow restrictor. A filter 306 may be disposed upstream of the bolus flow path 310 to filter the fluid before it enters the MEMS flow restrictor 314. Additional flow restrictors 314 may be disposed in the bolus flow path 310 upstream and/or downstream of the bolus delivery system 312. As shown in FIG. 2, the flow restrictor 314 may be omitted from the bolus flow path 310.

The parallel basal flow path 308 and the bolus flow path 310 join at a common channel 318, upstream of a cannula 320. The cannula 320 extends into/through the skin 322 of the user. In this way, the microfluidic circuit 300 provides a flowpath from the reservoir to user, for controlled delivery of the insulin or other fluid drug formulation subcutaneously to the user.

The microfluidic circuit 300 may include additional components. Conversely, certain components may be omitted. In any case, the microfluidic circuit 300 is configured to deliver one or more drugs in a liquid vehicle, e.g., as a solution or suitable suspension of a drug dissolved or dispersed in a pharmaceutically acceptable liquid excipient vehicle. The devices and systems described herein can be used to deliver essentially any suitable pharmaceutical agent for therapeutic, prophylactic, diagnostic, or palliative purposes.

FIGS. 4-7 illustrate some non-limiting examples of a MEMS flow restrictor 400 (or portions thereof) that may be incorporated into a microfluidic circuit, such as any of the ones described above.

The MEMS flow restrictor 400 includes a first substrate 402 attached to a second substrate 404. In some instances, the first substrate 402 and the second substrate 404 are attached to each other by way of anodic bonding. Any suitable MEMS attachment/sealing process or technique may be used.

The first substrate 402 includes a flow channel 406 configured to enable the flow of fluid therethrough. In some embodiments, the flow channel 406 is etched into the first substrate 402. The flow channel 406 may be a hermetic microchannel between the first substrate 402 and the second substrate 404 when the first substrate 402 and the second substrate 404 are attached/sealed to each other.

Figure 4:
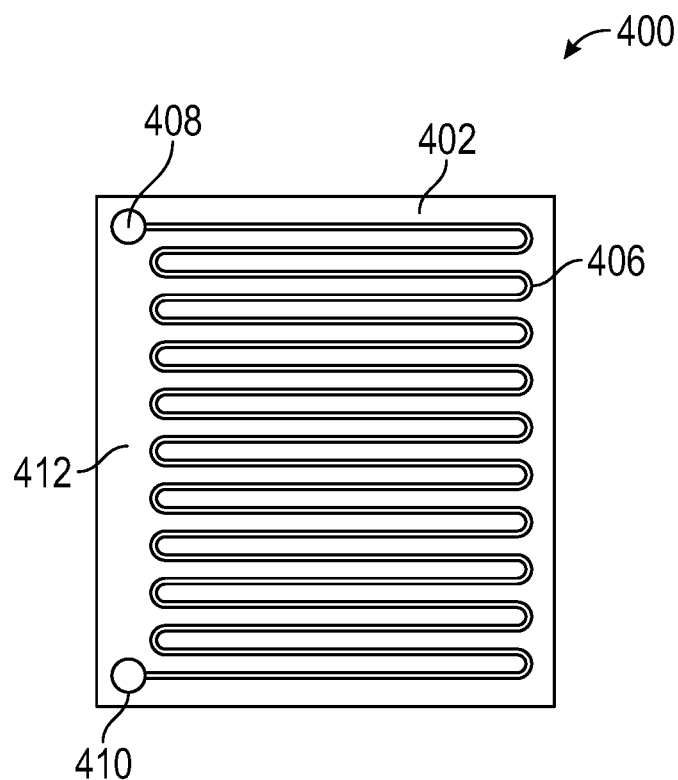
FIG. 4 is a plan view of an internal portion of a microelectromechanical system (MEMS) flow restrictor in accordance with one or more embodiments of the present disclosure.
Figure 5:
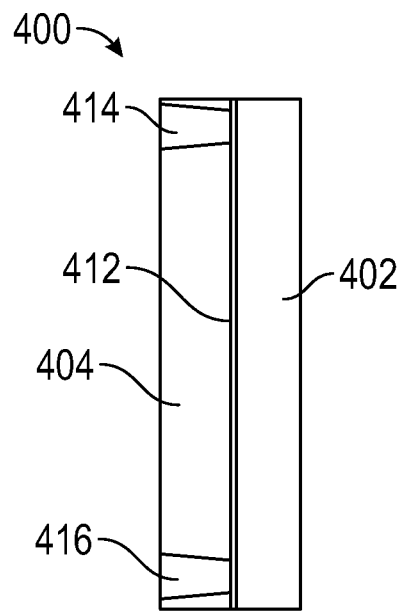
FIG. 5 is a cross-sectional view of one embodiment of the MEMS flow restrictor shown in FIG. 4.
Figure 7:
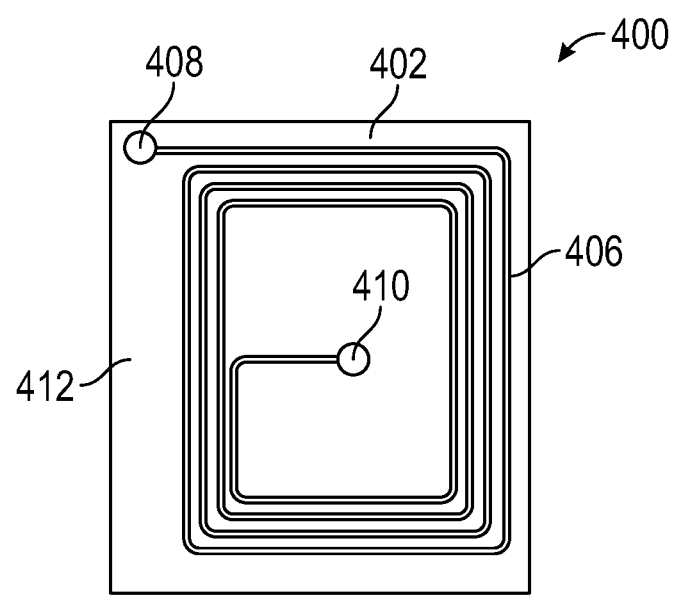
FIG. 7 is a plan view of a portion of a MEMS flow restrictor in accordance with one or more embodiments of the present disclosure.

The flow channel 406 includes an inlet 408 and an outlet 410 at each end of the flow channel. In some embodiments, as shown in FIGS. 4 and 7, the inlet 408 and the outlet 410 are disposed on the same surface 412 of the first substrate 402 as the flow channel 406. In this way, the central axes of the inlet and outlet openings may extend in a direction normal to the direction of flow within the flow channel. In such instances, the second substrate 404 may include an inlet opening 414 and an outlet opening 416 that correspond to the inlet 408 and the outlet 410, respectively. That is, the inlet 408 is in fluid communication with the inlet opening 414, and the outlet 410 is in fluid communication with the outlet opening 416. As illustrated in FIG. 5, the inlet opening 414 and the outlet opening 416 may pass through the thickness of the second substrate 404 and align respectively with the inlet 408 and the outlet 410. In this manner, the liquid drug formulation may flow (in a restricted manner) through the inlet opening 414, into the inlet 408, through the flow channel 406, out of the outlet 410, and through the outlet opening 416.

In various embodiments, the inlet opening 414 and the outlet opening 416 may be in fluid communication with a basal flow path or a bolus flow path of a microfluidic circuit.

In certain embodiments, the inlet opening 414 and the outlet opening 416 is tapered. For example, the inlet opening 414 may narrow towards the inlet 408, and the outlet opening 416 may expand from the outlet 410.

Figure 6:
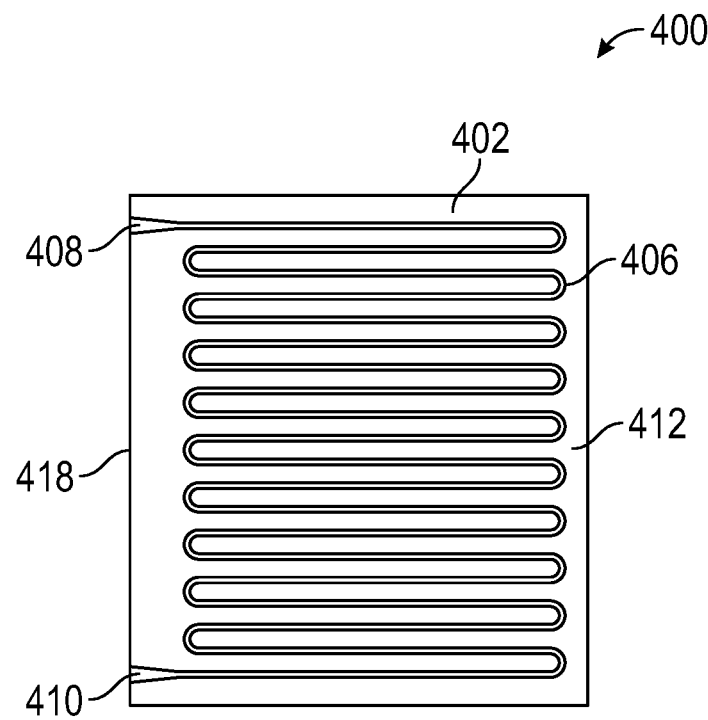
FIG. 6 is a plan view of a portion of a MEMS flow restrictor in accordance with one or more embodiments of the present disclosure.

In some other embodiments, as shown in FIG. 6, the inlet 408 and the outlet 410 of the flow channel 406 may be disposed on a side surface 418 relative to the surface 412 in which the flow channel 406 is etched into the first substrate 402. In this way, the central axes of the inlet and outlet openings may extend in a direction coinciding with (parallel to) a direction of flow within the flow channel. In such embodiments, the inlet opening 414 and the outlet opening 416 in the second substrate 404 may be omitted. In such embodiments, the inlet 408 and the outlet 410 may be in fluid communication with a basal flow path or a bolus flow path of a microfluidic circuit.

The inlet 408 and the outlet 410 may be tapered. Tapering of inlets and outlets in microfluidic flow restrictors is described in U.S. Patent Application Publication No. 2018/0177941, which is incorporated by reference herein in pertinent part.

The first substrate 402 and the second substrate 404 may be formed of various suitable materials, several of which are described herein. In some embodiments, the first and second substrates 402 and 404 are silicon, a glass, or a combination thereof. In one embodiment, the first and second substrates are silicon, such as from a silicon wafer used in a conventional microfabrication processing.

The flow channel 406 may take any of several different geometries. For example, the flow channel 406 may have a serpentine pattern, a decreasing/increasing spiral pattern, a decreasing/increasing square spiral pattern, or a combination thereof The flow channel may be formed in first substrate, in the second substrate, or in a combination of the first and second substrates. The flow channel 406 may be any size, shape, or configuration suitable to provide the desired flow restricting functionality in a microfluidic circuit as described herein. The cross-sectional area(s) and length of the flow channels are typical structural variables that may be selected/controlled to provide the desired flow restriction.

Figure 8:
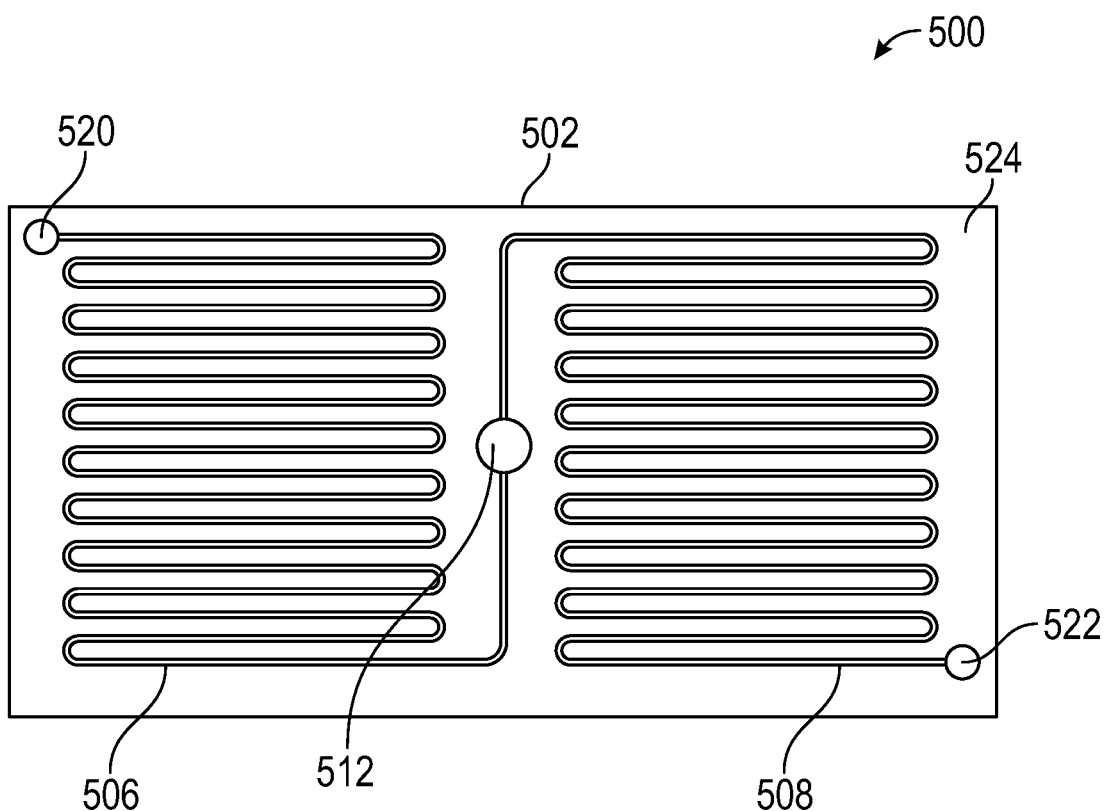
FIG. 8 is a plan view of an internal portion of a MEMS flow restrictor in accordance with one or more embodiments of the disclosure.
Figure 9:
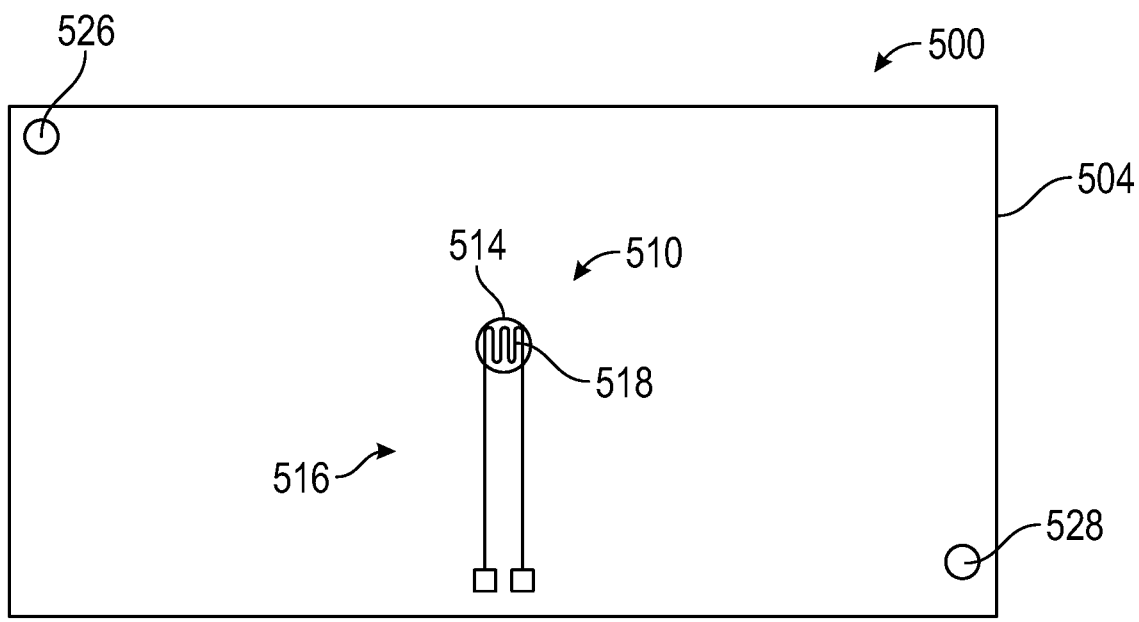
FIG. 9 is a plan view of one embodiment of a top/external portion of the MEMS flow restrictor shown in FIG. 8.

FIGS. 8 and 9 depict another embodiment of a MEMS flow restrictor 500. MEMS flow restrictor 500 is formed by a first substrate 502 and a second substrate 504. The first substrate 502 and the second substrate 504 may be attached to each other by anodic bonding or any other suitable MEMS attachment/sealing process or technique known in the art.

The MEMS flow restrictor 500 includes a first flow channel 506 and a second flow channel 508 formed in the first substrate 502. In this manner, the MEMS flow restrictor 500 is a single component having two flow restrictors. The first flow channel 506 and the second flow channel 508 are configured to enable the restricted flow of a liquid therethrough. In some embodiments, the first flow channel 506 and the second flow channel 508 are etched into the first substrate 502. The first flow channel 506 and the second flow channel 508 may form hermetic microchannels between the first substrate 502 and the second substrate 504 when the first substrate 502 and the second substrate 504 are attached/sealed to each other. The first flow channel 506 and the second flow channel 508 are in series with one another.

A pressure sensor 510 is disposed between the first flow channel 506 and the second flow channel 508. The pressure sensor 510 may be built into the flow restrictor 500. It may be integrally formed with the first substrate 502, the second substrate 504, or a combination thereof As shown in FIG. 8, the pressure sensor 510 includes a pressure chamber 512 disposed in the first substrate 502. For example, the pressure chamber 512 may be etched into the first substrate 502. In some instances, the pressure chamber 512 may be spherical, hemi-spherical, or the like. The pressure chamber 512 may be any suitable size, shape, or configuration. The pressure chamber 512 is disposed between and in fluid communication with the first flow channel 506 and the second flow channel 508. The portion of the first flow channel 506 leading into the pressure chamber 512 may be tapered, expanding into the pressure chamber 512. Similarly, the portion of the second flow channel 508 leaving the pressure chamber 512 may be tapered, narrowing towards the second flow channel 508.

The pressure sensor 510 also includes a pressure dome 514 (or membrane) disposed in or about the second substrate 504. In some instances, the pressure dome 514 comprises a region of the second substrate 504 that is thinner than the rest of the second substrate 504. The pressure dome 514 is disposed about, e.g., is adjacent to, the pressure chamber 512 when the first substrate 502 is attached to the second substrate 504.

The thinner region (i.e., the pressure dome 514) is configured to deflect due to a change in pressure within the pressure chamber 512. An operably associated strain gauge, or the like, is provided to detect, or measure, such deflection. For example, here two sensor wires 516 are in communication with a strain gauge 518 disposed on the pressure dome 514. In this manner, a change in fluid pressure within the pressure chamber 512 effective to displace the pressure dome 514 will be detected by the strain gauge 518. In some alternative embodiments, the pressure chamber 512 is omitted, and the change in pressure between the first flow channel 506 and the second flow channel 508 deflects the pressure dome 514.

The first flow channel 506 includes an inlet 520, and the second flow channel 508 include an outlet 522. In the illustrated embodiment, the inlet 520 and the outlet 522 are disposed on the same surface 524 of the first substrate 502 as the first flow channel 506 and the second flow channel 508. The second substrate 504 includes an inlet opening 526 and an outlet opening 528 that correspond to the inlet 520 and the outlet 522, respectively. For example, the inlet opening 526 and the outlet opening 528 may pass through the thickness of the second substrate 504 and align, respectively, with the inlet 520 and the outlet 522. In this manner, a liquid drug formulation may flow through the inlet opening 526, into the inlet 520, through the first flow channel 506, through the pressure chamber 512, through the second flow channel 508, out of the outlet 522, and through the outlet opening 528. In various embodiments, the inlet opening 526 and the outlet opening 528 may be in fluid communication with a basal flow path or a bolus flow path of a microfluidic circuit, as described herein.

The inlet opening 526 and the outlet opening 528 may be tapered. For example, the inlet opening 526 may narrow towards the inlet 520, and the outlet opening 528 may expand from the outlet 522. Tapering of inlets and outlets in microfluidic flow restrictors is described in U.S. Patent Application Publication No. 2018/0177941.

In some alternative embodiments, unlike the one shown in FIG. 8, the inlet 520 and the outlet 522 are disposed on different side surfaces relative to the surface 524 on which the first flow channel 506 and the second flow channel 508 are formed in the first substrate 502. In such embodiments, the inlet opening 526 and the outlet opening 528 in the second substrate 504 may be omitted. In such embodiments, the inlet 520 and the outlet 522 may be in fluid communication with a basal flow path or a bolus flow path of a microfluidic circuit. In certain embodiments, the inlet 520 and the outlet 522 may be tapered.

The first substrate 502 and the second substrate 504 may be formed of various suitable materials, several of which are described herein. In some embodiments, the first and second substrates 502 and 504 are silicon, a glass, or a combination thereof. In one embodiment, the first and second substrates are silicon, such as from a silicon wafer used in a conventional microfabrication processing.

The first flow channel 506 and the second flow channel 508 may take any of several different geometries. For example, the first flow channel 506 and the second flow channel 508 each may have a serpentine pattern, a decreasing/increasing spiral pattern, a decreasing/increasing square spiral pattern, or a combination thereof. In some embodiments, the first flow channel 506 and the second flow channel 508 have different patterns from one another.

The first flow channel 506 and the second flow channel 508 may be formed in first substrate 502, in the second substrate 504, or in a combination of the first and second substrates. The first flow channel 506 and the second flow channel 508 may be any size, shape, or configuration suitable to provide the desired flow restricting functionality in a microfluidic circuit as described herein. The cross-sectional area(s) and length of the flow channels are typical structural variables that may be selected/controlled to provide the desired flow restriction Modifications and variations of the methods and devices described herein will be obvious to those skilled in the art from the foregoing detailed description. Such modifications and variations are intended to come within the scope of the appended claims.

That which is claimed is:

1. A device for administering a liquid drug formulation to a patient, the device comprising:
   a reservoir configured to hold a quantity of the liquid drug formulation; and
   a microfluidic circuit which comprises at least one flow path configured to transport the liquid drug formulation from the reservoir to a drug release outlet,
   wherein the at least one flow path comprises a pressure sensor disposed between a first flow restrictor comprising a first flow channel having an inlet and a second flow restrictor comprising a second flow channel having an outlet in the at least one flow path, wherein each of the first flow restrictor and the second flow restrictor is not a microcapillary, and wherein each of the inlet and the outlet are tapered,
   wherein the pressure sensor, the first flow restrictor, and the second flow restrictor are disposed in a first substrate such that each of the first flow channel and second flow channel have a closed, elongated bottom wall, an elongated opening in a planar surface of the first substrate opposed to the bottom wall, and a pair of elongated sidewalls extending between the bottom wall of the flow channel and the elongated opening, the elongated opening closed off by a second substrate, and
   wherein the pressure sensor comprises (i) a pressure chamber formed into the first substrate and disposed between the first flow channel and the second flow channel, (ii) a pressure dome adjacent to the pressure chamber and disposed between the first flow restrictor and the second flow restrictor, the pressure dome comprising a first region of the second substrate that is thinner than each of a second region of the second substrate that covers the first flow channel and a third region of the second substrate that covers the second flow channel, and (iii) a strain gauge disposed about the pressure dome.

2. The device of claim 1, wherein the device is in the form of a patch pump configured to be worn on the patient's skin, and wherein the liquid drug formulation comprises insulin.

3. The device of claim 1, wherein the first flow channel comprises a microfabricated flow channel formed into the first substrate and disposed between the first substrate and the second substrate, and the second flow channel comprises a microfabricated flow channel formed into the first substrate and disposed between the first substrate and the second substrate.

4. The device of claim 1, wherein the first substrate and the second substrate comprise silicon.

5. The device of claim 1, wherein the first substrate and the second substrate are anodically bonded together.

6. The device of claim 1, wherein each of the first flow channel and the second flow channel is in a serpentine pattern, a spiral pattern, or a square pattern, across the first substrate.

7. The device of claim 1, wherein each of the first flow channel and the second flow channel is formed by a microfabrication process.

8. A method for administering a drug in fluid form to a patient, the method comprising:
   providing the device of claim 1 with the reservoir filled with the liquid drug formulation;
   permitting flow of the liquid drug formulation from the reservoir and into the at least one flow path; and
   restricting the flow of the liquid drug formulation through the at least one flow path using at least one of the first flow restrictor and the second flow restrictor.

9. The device of claim 1, wherein the at least one flow path is a basal flow path, and wherein the microfluidic circuit further comprises a bolus flow path in parallel to the basal flow path.

10. The device of claim 9, wherein the first flow restrictor and the second flow restrictor are disposed in series along the basal flow path, and wherein the pressure sensor is configured to detect the pressure of fluid in the basal flow path.

11. The device of claim 10, wherein each of the first flow channel and the second flow channel comprises a microfabricated flow channel formed into the first substrate and disposed between the first substrate and the second substrate.

12. The device of claim 1, wherein the inlet is connected to an upstream portion of the microfluidic circuit which connects to the reservoir, and wherein the outlet is connected to a downstream portion of the microfluidic circuit which connects to the drug release outlet.

13. The device of claim 12, further comprising:
   a fill port connected to the upstream portion of the microfluidic circuit and configured to enable filling the reservoir with the quantity of the liquid drug formulation; and
   a filter connected to the upstream portion of the microfluidic circuit and configured to filter the liquid drug formulation flowing from the reservoir before it enters the inlet,
   wherein the drug release outlet is connected to a cannula configurable for subcutaneous administration of the liquid drug formulation to the patient.

14. A pump device for subcutaneous administration of insulin to a patient, the device comprising:
   a reservoir configured to hold a quantity of insulin;
   a cannula for subcutaneous insertion to the patient;
   a microfluidic circuit which comprises a basal flow path and a bolus flow path, and which is configured to transport the insulin from the reservoir to the cannula; and
   a first flow restrictor in the basal flow path comprising a first flow channel having an inlet, and a second flow restrictor in the basal flow path comprising a second flow channel having an outlet, the first flow channel and second flow channel formed in a first substrate and disposed between the first substrate and a second substrate, wherein each of the first flow channel and second flow channel have a closed, elongated bottom wall, an elongated opening in a planar surface of the first substrate opposed to the bottom wall, and a pair of elongated sidewalls extending between the bottom wall of the flow channel and the elongated opening, the elongated opening closed off by the second substrate, wherein each of the first flow restrictor and the second flow restrictor is not a microcapillary, and wherein each of the inlet and outlet are tapered; and at least one pressure sensor disposed between the first flow restrictor and the second flow restrictor, the at least one pressure sensor being configured to detect the pressure of fluid in the basal flow path, wherein the at least one pressure sensor is integral with the first substrate, the second substrate, or a combination thereof, wherein the at least one pressure sensor comprises (i) a pressure chamber formed into the first substrate and disposed between the first flow channel and the second flow channel, (ii) a pressure dome that adjacent to the pressure chamber and disposed between the first flow restrictor and the second flow restrictor, the pressure dome comprising a first region of the second substrate that is thinner than each of a second region of the second substrate that covers the first flow channel and a third region of the second substrate that covers the second flow channel and (iii) a strain gauge disposed about the pressure dome.

15. The pump device of claim 14, wherein at least one of the first flow channel and the second flow channel is formed by a microfabrication process.

16. A method for administering insulin to a patient, the method comprising:
providing the pump device of claim 14 with the reservoir filled with insulin;
permitting flow of insulin from the reservoir and into the basal flow path; and
restricting the flow of the insulin through the basal flow path using the first flow restrictor and the second flow restrictor.

17. A method of making a pair of flow restrictors, the method comprising:
forming a first flow channel having an inlet and a second flow channel having an outlet into a surface of a first substrate such that each of the first flow channel and second flow channel have a closed, elongated bottom wall, an elongated opening in a planar surface of the first substrate opposed to the bottom wall, and a pair of elongated sidewalls extending between the bottom wall of the flow channel and the elongated opening, wherein each of the inlet and the outlet are tapered;

attaching a second substrate to the surface of the first substrate such that the elongated opening of each of the first flow channel and the second flow channel are closed off by the second substrate, to thereby form a first flow restrictor and a second flow restrictor between the first substrate and the second substrate, wherein the first flow restrictor comprises the first flow channel, and wherein the second flow restrictor comprises the second flow channel, wherein each of the first flow restrictor and the second flow restrictor is not a microcapillary; and forming a pressure sensor disposed between the first flow restrictor and the second flow restrictor, wherein the pressure sensor is in fluid communication with each of the first flow channel and the second flow channel, wherein the pressure sensor comprises (i) a pressure chamber formed into the first substrate and disposed between the first flow channel and the second flow channel, (ii) a pressure dome adjacent to the pressure chamber and disposed between the first flow restrictor and the second flow restrictor, the pressure dome comprising a first region of the second substrate that is thinner than each of a second region of the second substrate that covers the first flow channel and a third region of the second substrate that covers the second flow channel and (iii) a strain gauge disposed about the pressure dome, wherein the first flow channel comprises an inlet and the second flow channel comprises an outlet of the attached first and second substrates, the inlet and the outlet being configured for operable connection into a flow path of a microfluidic circuit, and wherein each of the first flow channel and the second flow channel is dimensioned to throttle a flow of fluid through the flow path of the microfluidic circuit.

18. The method of claim 17, wherein forming the first flow channel and the second flow channel comprises etching the surface of the first substrate.

19. The method of claim 17, wherein at least one of the first substrate and the second substrate comprises silicon.

20. The method of claim 17, wherein attaching-of the second substrate to the surface of the first substrate comprises anodic bonding the first substrate and the second substrate to one another.

21. The method of claim 17, wherein each of the first flow channel and the second flow channel is in a serpentine pattern, a spiral pattern, or a square pattern, across the first substrate.

* * * * *